United States Patent [19]

Walsdorf et al.

[11] Patent Number: 4,726,952
[45] Date of Patent: Feb. 23, 1988

[54] SLOW-RELEASE SODIUM FLUORIDE TABLET, METHOD OF MAKING, AND METHOD OF TREATMENT OF OSTEOPOROSIS

[75] Inventors: Neill B. Walsdorf, San Antonio; Charles Y. C. Pak, Dallas, both of Tex.

[73] Assignees: Mission Pharmacal, San Antonio; Board of Regents, University of Texas System, Austin, both of Tex.

[21] Appl. No.: 842,304

[22] Filed: Mar. 21, 1986

Related U.S. Application Data

[63] Continuation-in-part of Ser. No. 522,014, Aug. 11, 1983, abandoned.

[51] Int. Cl.⁴ .................. A61K 9/22; A61K 9/26; A61K 33/16
[52] U.S. Cl. .................. 424/476; 424/151; 424/498; 424/502
[58] Field of Search .................. 424/19–22, 424/38, 151, 476, 498, 502

[56] References Cited

U.S. PATENT DOCUMENTS

| Re. 24,090 | 11/1955 | Diamond | 424/22 |
|---|---|---|---|
| 3,062,270 | 11/1962 | Costello | 424/22 |
| 3,108,046 | 10/1963 | Harbit | 424/38 |
| 3,279,998 | 10/1966 | Raff et al. | 424/22 |
| 3,402,240 | 9/1968 | Cain et al. | 424/38 |
| 3,577,514 | 5/1971 | Robinson | 424/22 |
| 4,104,370 | 8/1978 | Bloch | 424/19 |
| 4,169,885 | 10/1979 | Raaf et al. | 424/52 |

OTHER PUBLICATIONS

Ekstrand et al., Europ. J. Clin. Pharmacol. 12:311–317, (1977), "Pharmacokinetics of Fluoride in Man After Single and Multiple Oral Doses".
Hasvold and Ekren, Eur. J. Clin. Pharmacol., vol. 19, pp. 225–230, (1981).

*Primary Examiner*—Shep K. Rose
*Attorney, Agent, or Firm*—Arnold, White & Durkee

[57] ABSTRACT

A novel use for a slow-release sodium fluoride preparation. Such slow-release sodium preparation is shown to provide a safe but effective level of fluoride in serum, optimal for the treatment of osteoporosis. It minimizes gastrointestinal side effects by limiting the amount of fluoride released in the stomach and it reduces rheumatic complications by avoiding toxic levels of fluoride in serum. The amount of fluoride absorbed is nevertheless sufficient to stimulate bone formation and prevent fractures. Thus, the maintenance of serum fluoride as encompassed in this invention, allows for a safe and effective treatment of osteoporosis.

5 Claims, 2 Drawing Figures

SLOW-RELEASE SODIUM FLUORIDE TABLET, METHOD OF MAKING, AND METHOD OF TREATMENT OF OSTEOPOROSIS

Developmental work relating to part of the present invention was supported by grants from the U.S. government National Institutes of Health (POI-AM 20543 and R01-AM 16061).

This application is a continuation-in-part of co-pending application Ser. No. 522,014, filed on Aug. 11, 1983, now abandoned, and expressly incorporated by reference herein.

BACKGROUND OF THE INVENTION

Osteoporosis is a common disabling bone disease, particularly in post-menopausal women. Gradual loss of bone makes it porous and weak. Fracture of spine, hip and forearm frequently develop even without significant trauma.

Once the osteoporotic disease has developed, so much bone mass may already have been lost such that treatments directed at preventing further bone loss (for example, calcium supplements) would likely be of limited value. An ideal goal of therapy is patients with established osteoporosis with fracture is to provide a treatment program that will increase bone mass and restore "lost" bone. Unfortunately, most available treatment programs have failed to augment bone mass (Pak, The Menopause, Edit. J. J. Buchsbaum Springer-Verlag, 1983, pp. 35-54).

Sodium fluoride may be one agent capable of making more bone in osteoporosis. This possibility was first recognized in 1932, when Moller and Gudjonsson noted skeletal sclerosis in subject with overexposure with cryolite rich in fluoride (Acta Radiol., Vol. 13, 1932, pp. 269-294). It is now known that fluoride causes proliferation and increases the activity of osteoblasts, cells responsible for bone formation (Farley et al., Science, Vol. 222, 1983, pp. 330-332). When fluoride alone is given to patients with esteoporosis, the newly-formed bone is poorly mineralized (that is, deficient in calcium phosphate). However, when adequate calcium supplementation is provided along with fluoride, formation of mineralized bone may be stimulated (Jowsey et al., Amer. J. Med., Vol. 53, 1972, pp. 43-49). Using sodium fluoride (50-60 mg/day) with calcium supplement (800-1500 mg elemental calcium/day), formation of new bone has been shown on actual microscopic examination of biopsied bone (Briancon and Meunier, Orthop. Clin. North Amer., Vol. 12, 1981, pp. 629-648). Moreover, the rate of bone fracture was shown to be significantly reduced by treatment, compared to that of the untreated group (Riggs et al., N. Engl. J. Med., Vol. 306, 1982, pp. 446-450). Thus, there are sufficient references to suggest that long-term treatment with sodium fluoride could be effective in treating established osteoporosis.

Unfortunately, sodium fluoride has been associated with frequent adverse reactions. In several long-term trials, gastrointestinal side-effects (nausea, vomiting, diarrhea, bleeding) occurred in 16-50% of patients and rheumatic complications (painful foot and knee due to synovitis and plantar fascial syndrome) occurred in 17-32% (Table 1).

TABLE 1

| SIDE EFFECTS OF CONVENTIONAL SODIUM FLUORIDE | | |
| --- | --- | --- |
| Side Effects | Authors | Percentage of Patients |
| Gastrointestinal | Riggs et al. (1980) | 19.4 |
| | Riggs et al. (1982) | 16.4 |
| | Briancon and Meunier (1981) | 21.5 |
| | von Kesteren et al. (1982) | 50.0 |
| Rheumatic | Riggs et al. (1980) | 30.6 |
| | Riggs et al. (1982) | 23.0 |
| | Briancon and Meunier (1981) | 32.4 |
| | Franke et al. (1974) | 17.4 |

These complications have precluded the widespread acceptance of sodium fluoride for the treatment of osteoporosis. It should be noted that above clinical trials were conducted with plain or acid resistant form of sodium fluoride. To the best of our knowledge, a slow-release form of sodium fluoride, as embodied in this invention, has never been used for the long-term treatment of osteoporosis.

It is our contention that the special embodiments of our invention conferring slow-release characteristic to the oral sodium fluoride preparations result in protection against above-mentioned side effects of conventional preparations so far used, while providing sufficient fluoride absorption to confer beneficial effect on bone. Evidence for this contention will be provided in this continuation-in-part in the following section (Special Embodiment . . .) and illustrated by Examples to follow.

PREFERRED EMBODIMENTS OF THE PRESENT INVENTION

Figure 1:
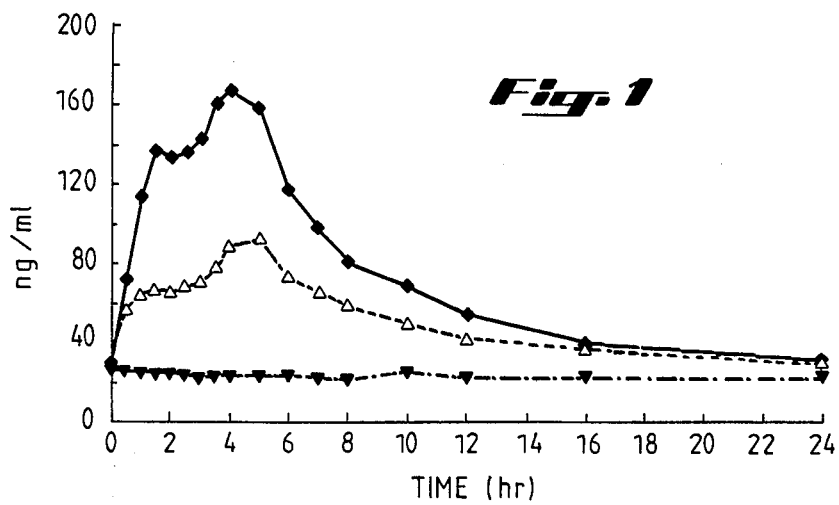
FIG. 1 shows the mean serum fluoride level of 5 normal volunteers after administration of slow-release sodium fluoride (Δ), rapid release sodium fluoride (♦) or placebo (▼).

The parent application Ser. No. 06/522,014 described a novel method for making a slow-release tablet preparation of sodium fluoride to be used for the treatment of osteoporosis. It was presumed that, owing to its slow-release nature, this particular form of sodium fluoride would be safe to use and yet be therapeutically effective. On July 22, 1982, Dr. Charles Y. C. Pak, Professor of Medicine at the University of Texas Health Science Center at Dallas, obtained an investigational new drug status (IND 20,612) from the Food and Drug Administration for the study of this drug in osteoporosis. Since that time clinical studies with slow-release sodium fluoride have been conducted. Results obtained in these studies as shown below, have now confirmed predictions of the parent patent application Ser. No. (06/522,014). The present application establishes more firmly the effective and safe use of slow-release sodium fluoride in the treatment of osteoporosis.

The slow-release sodium fluoride formulation of the present invention comprises a dose form, preferably a tablet, resistant to dissolution by gastric secretions but being gradually drained of sodium fluoride in an intestinal environment. The expectation that our specific formulation providing slow-release fluoride would avoid the complications of sodium fluoride therapy was derived from our understanding of why these complications occur. The gastrointestinal side-effects are due to the corrosion of the intestinal lining (particularly of the stomach) (Eichler et al., Intern. J. Clin. Pharm., Vol. 20, 1982, pp. 334-338). The rheumatic complications result when fluoride is rapidly absorbed, allowing the bone concentration to reach the toxic level and causing acute skeletal fluorosis (formation of abnormal bone rich in fluoride near affected joints). The lower limit of the toxic level in serum has been set at 10 uM (or 190 ng/ml), since fluorosis has been reported above this concentration (Taves, Fed. Proc., Vol. 29, 1970, pp. 1185-1187).

From above considerations, it became apparent to us that oral sodium fluoride preparations which rapidly release fluoride would be particularly prone to cause adverse reactions. Sufficient amounts of hydrofluoric acid could form from the reaction of the released fluoride with the gastric hydrochloric acid to corrode the stomach lining. Moreover, since hydrofluoric acid is avidly absorbed in the stomach (Whitford and Pashley, Calc. Tiss. Intern., Vol. 36, 1984, pp. 302-307), fluoride absorption may be sufficiently rapid to allow the toxic limit in serum to be exceeded.

The Conventional sodium fluoride preparations used in available long-term clinical trials were not slow-release preparations as in our invention. They were plain preparations or enteric coated preparations which, despite being sometimes administered with food or calcium supplements to reduce gastric irritation, probably caused sufficiently rapid fluoride release to cause the complications enumerated above.

The failure of others to try truly slow-release preparations of sodium fluoride is probably due to the fear that insufficient amount of fluoride would be absorbed. The prior art would have taught so, since the slow-release preparation would limit the formation of hydrofluoric acid, recognized heretofore to be the predominant fluoride species which is absorbed from the intestinal tract (Whitford and Pahsley, Calc. Tiss. Intern., Vol. 36, 1984 pp. 302-307). Thus, using the customary dose of sodium fluoride (50 mg/day), the amount of fluoride absorbed was expected to be too low to exert a therapeutic effect on bone. It is believed that at least 5 uM or 95 ng/ml concentration of fluoride in serum must be reached to cause bone growth (Taves, Fed. Proc., Vol. 29, 1970, pp. 1185-1187). The prior art would have taught that this therapeutic concentration would not have been reached using a slow-release preparation. The present slow-release sodium fluoride formulation is preferably a tablet resistant to gastric dissolution but being gradually drained of sodium fluoride in an intestinal environment.

Clinical studies by the present inventors using a slow-release formulation of sodium fluoride made according to specifications of this invention have disclosed a surprising discovery. This discovery is that the use of this preparation at a customary dose of 50 mg/day is associated with minimum gastrointestinal and rheumatic complications, and yet provides sufficient fluoride absorption to keep the fasting serum fluoride level within the desired "therapeutic window" (above therapeutic threshold concentration (qo mg/nl) but below the toxic concentration (lqo mg/nl)). The slow-release sodium fluoride formulation of the present invention is adopted to gradually release sodium fluoride in the small intestine. Generally a 25 mg slow-release formulation gradually releases its sodium fluoride between about 1 and 25 hours after administration.

When 5 normal subjects were orally administered a single dose of slow-release sodium fluoride, the serum concentration of fluoride gradually rose, reaching a peak at 5-6 hours (Example 1). Thereafter it gradually declined. The results suggested a slow but sustained absorption of fluoride, and indicated a discovery that fluoride may be absorbed as the anionic form in the intestine in lieu of the formation and absorption as hydrofluoric acid in the stomach.

Forty-one patients with osteoporosis were orally administered slow-release sodium fluoride at a dosage of 25 mg/twice/day orally (with crackers) intermittently (at 3-month intervals, separated by 2 months without treatment, repeated continuously). Fasting serum fluoride obtained during treatment was maintained within the therapeutic window (Example 2). Thus, serum fluoride on treatment was above the lower limit of therapeutic level (95 ng/ml) but below the toxic concentration (190 ng/ml).

A total of 86 osteoporotic patients have so far received orally administered slow-release sodium fluoride over a mean period of 14.9 months (Example 3). The only gastrointestinal side effect was nausea in 4.7% of patients and the only rheumatic complication was mild plantar fasciitis in 2.3% of patients. These figures are much lower than those reported with enteric-coated or plain preparations of sodium fluoride (see Table 1). Thus, the present invention minimizes gastrointesinal hazards by limiting the amount of fluoride released to form corrosive hydrofluoric acid in the stomach. It also reduces rheumatic complications by preventing toxic levels of fluoride from being reached in blood, thus averting chances for the development of fluorosis.

Additional studies were conducted to determine if the maintenance of serum fluoride level within the therapeutic window has a desired beneficial effect on bone in osteoporosis. Serum osteocalcin is believed to be a marker for bone forming activity (Zerwekh et al., J. Clin. Enoc. Metab., Vol. 60, 1985, pp. 615-617). During long-term intermittent therapy with slow-release sodium fluoride (3 months out of every 5 months), serum osteocalcin progressively rose, reaching significance by 18.5 months (Example 4). Thus, the rise in serum fluoride to the therapeutic level is exerting appropriate physiological action on bone.

In 10 patients with postmenopausal osteoporosis and receiving orally administered sodium fluoride (slow-release formalation) continuously for 12 months at a dose of 25 mg twice/day, spinal bone density was measured by dual photon absorptiometry (Example 5). The bone density progressively increased. In 44 patients receiving slow-release sodium fluoride over an average duration of 14.2 months, only two patients sustained a fracture (of spine) (Example 6). Thus, slow-release sodium fluoride appears to be effective in making more bone and in averting new fractures.

The following examples are included to further describe preferred embodiments of the present invention and are not intended to limit the invention unless otherwise specifically indicated in the claims appended hereto.

EXAMPLE 1

Sodium Fluoride Bioavailabilty

In 5 normal volunteers, serum fluoride was measured at various times during the 24 hours following an oral administration of 25 mg each of slow-release sodium fluoride (Δ), plain (rapid release) sodium fluoride (♦) or placebo (without fluoride) (▼).

There was no significant change in serum fluoride following placebo administraiton (FIG. 1). Serum fluoride reached a high level rapidly following administration of plain sodium fluoride. However, there was a more gradual rise in serum fluoride, with avoidance of such a high rapidly occuring peak of serum fluoride, following administration of sodium fluoride in the slow-release form. Twelve hours after slow-release sodium fluoride administration, serum fluoride level was significantly higher than in the basal state (placebo level).

Thus, a sustained elevation in serum fluoride level, with avoidance of high peaks, could be achieved with the slow-release sodium fluoride preparation. The more gradual rise in serum fluoride level with the slow-release preparation suggests that the fluoride ion is only slowly released into the gastric juice.

EXAMPLE 2

Manitenance of Serum Fluoride Within Therapeutic Window During Long-Term Slow-Release Sodium Fluoride Therapy In 41 patients with osteoporosis, slow-release sodium fluoride was given orally at a dosage of 25 mg twice/day for 3 months out of every 5 month cycle.

Figure 2:
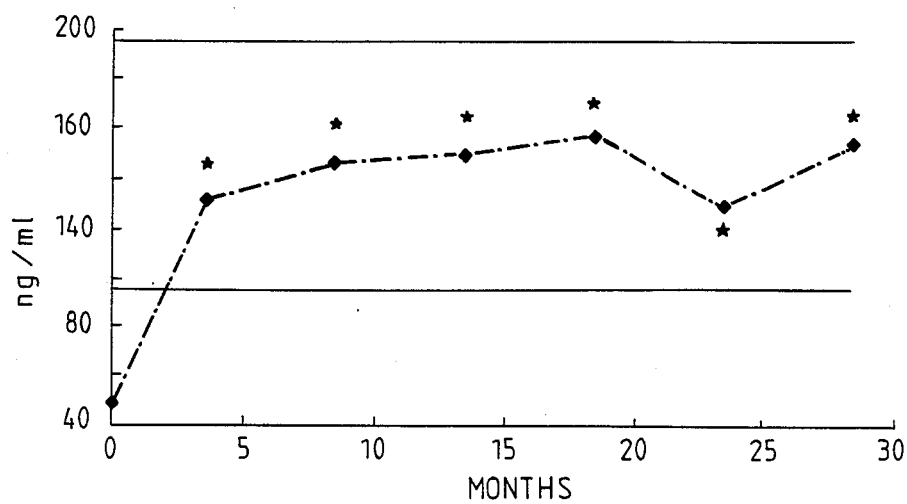
FIG. 2 shows the mean serum fluoride level of 41 patients with osteoporosis being administered slow-release sodium fluoride.

Serum fluoride level rose significantly ($*=p<0.05$) during treatment (FIG. 2). The treated values were above the lower limit of therapeutic range (95 ng/ml) and below the toxic level (190 ng/ml). It is generally blieved that serum level of at least 95 ng/ml must br reached to exert beneficial effect on bone, and that toxic systemic side effects (e.g. rheumatic symptoms) appear when serum fluoride level exceeds 190 ng/ml.

Thus, the long-term use of slow-release sodium fluoride provides a sustained maintenance of therapeutic but safe levels of serum fluoride.

EXAMPLE 3

Adverse Reaction to Slow-Release Sodium Fluoride

Eighty-six osteoporotic patients received slow-release sodium fluoride for a cumulative period of 1,281 months. Adverse reactions were uncommon and minor (Table 2).

The only gastrointestinal side effect noted was nausea in 4 patients (4.7%). Although two patients had positive test for occult blood in stool, the origin of blood loss was due to hemorrhoids in one and dental extraction in the other. Two patients (2.3%) had plantar fascitis which resolved upon reduction of sodium fluoride dosage. In contrast, other workers reported a much higher incidence of gastrointestinal and rheumatic complications using non-slow-release sodium fluoride preparations (Table 1).

The reduced gastrointestinal side effects observed with the use of slow-release sodium fluoride could be explained by the avoidance of the excessive gastric formation of corrosive hydrofluoric acid due to the slow-release nature of the product essentially bypassing the stomach. The low incidence of rheumatic complication could be due to the avoidance of high levels of fluoride in serum.

TABLE 2

| SIDE EFFECTS OF SLOW-RELEASE NaF | | |
|---|---|---|
| Symptoms | No. Patients | % |
| Gastrointestinal | 0 | 0 |
| Vomiting | 0 | 0 |
| Belching | 0 | 0 |
| Diarrhea | 0 | 0 |
| Pain/cramp | 0 | 0 |
| Melena | 0 | 0 |
| Dyspepsia | 0 | 0 |
| Anorexia | 0 | 0 |
| Nausea | 4 | 4.7 |
| Bleeding | 0 | 0 |
| Rheumatic | | |
| Plantar fascitis | 2 | 2.3 |
| Synovitis | 0 | 0 |

EXAMPLE 4

Long-Term Effect of Slow-Release Sodium Fluoride Therapy on Serum Osteocalcin Serum osteocalcin is believed to be a marker of osteoblastic (bone-forming) activity.

Following administration of slow-release sodium fluoride 25 mg twice/day for 3 months out of every 5 month cycle in 17 osteoporotic patients, serum osteocalcin level obtained during treatment gradually increased, reaching significance at later periods of treatment (Table 3).

Thus, sufficient fluoride must have been absorbed to exert its expected physiological action on bone.

TABLE 3

| SERUM OSTEOCALCIN LEVELS | |
|---|---|
| Prior level-<br>Sodium Fluoride | Serum Osteocalcin<br>ng/ml |
|  | 4.1 ± 0.5 |
| 3.5 mo. | 4.4 ± 0.4 |
| 8.5 mo. | 4.6 ± 0.3 |
| 13.5 mo. | 4.7 ± 0.5 |
| 18.5 mo. | 5.1 ± 0.4* |
| 23.5 mo. | 5.7 ± 0.6* |

*$p < 0.05$

EXAMPLE 5

Effect of Long-Term Slow-Release NaF Therapy on Vertebral Bone Density

In 10 patients with postmemopausal osteoporosis, slow-release sodium fluoride was provided at a dosage of mg twice/day on a long-term basis (continuously for 13 months). The fractional change in bone density was +0.032±0.027 SE at 6 months of treatment, and +0.082±0.057 SE at 12 months. Thus, sodium fluoride therapy (slow-release) may augment vertebral bone mass, whereas the expected finding without treatment would be a decline in bone density (mass).

EXAMPLE 6

Effect of Long-Term Slow-Release NaF Treatment on Skeletal Fracture

Forty-four patients received slow-release sodium fluoride 25 mg twice/day for an average duration of 14.2 months.

None had non-traumatic fracture of the distal forearm or proximal femur during treatment. Two patients had fracture of vertebrae during treatment (5 sites in one, one in the other). No other had fracture. The fracture incidence was therefore 115/1000 patient-yr during treatment, much lower than the reported fracture incidence in untreated osteoporotic patients of 834/1000 patient-yr (Riggs et al., N. Engl. J, Med., Vol. 306, 1982, pp. 446–450).

Thus, slow-release sodium fluoride is effective in preventing new fractures in postmenopausal osteoporotic women.

Changes may be made in the formulations and procedures described herein without departing from the concept and scope of the invention as defined in the following claims.

What is claimed is:

1. In a process for the treatment of patients having osteoporosis comprising orally administering to said patients about 50 mg sodium fluoride per day the improvement consisting essentially of the step of administering 25 mg. of sodium fluoride twice a day, to maintain a serum fluoride concentration at a therapeutic level above 95 ng/ml and less than about 190 ng/ml; each 25 mg. sodium fluoride dose being in a slow-release sodium fluoride carnauba wax formulation adopted to gradually release sodium fluoride in the small intestine.

2. The process of claim 1, wherein the osteoporosis is defined as being that of a post-menopausal woman.

3. The process of claim 1, wherein the osteoporosis is defined as being that of an elderly man.

4. The process of claim 1, wherein the osteoporosis may have resulted from causes, such as steroid excess or be idiopathic.

5. The process for claim 1, wherein the osteoporosis is defined as involving osteopenia (bone loss) but no facture.

* * * * *

UNITED STATES PATENT AND TRADEMARK OFFICE
CERTIFICATE OF CORRECTION

PATENT NO. : 4,726,952

DATED : February 23, 1988

INVENTOR(S) : Neill B. Walsdorf and Charles Y. C. Pak

It is certified that error appears in the above-identified patent and that said Letters Patent is hereby corrected as shown below:

Column 7, line 17 after the word "day" please insert a comma --,--.

Column 8, line 3, delete "95" and insert therefore --90--.

Column 8, line 6, delete "adopted" and insert therefore --adapted--.

Column 8, line 17, delete "facture" and insert therefore --fracture--.

Signed and Sealed this

Ninth Day of August, 1988

*Attest:*

*Attesting Officer*

DONALD J. QUIGG

Commissioner of Patents and Trademarks